(12) United States Patent
Cox

(10) Patent No.: US 11,304,718 B2
(45) Date of Patent: *Apr. 19, 2022

(54) SYSTEM FOR TISSUE DISSECTION AND RETRACTION

(71) Applicant: John A. Cox, San Clemente, CA (US)

(72) Inventor: John A. Cox, San Clemente, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/922,609

(22) Filed: Oct. 26, 2015

(65) Prior Publication Data

US 2016/0038172 A1    Feb. 11, 2016

Related U.S. Application Data

(63) Continuation of application No. 13/220,461, filed on Aug. 29, 2011, now Pat. No. 9,168,053, which is a
(Continued)

(51) Int. Cl.
| | |
|---|---|
| *A61B 17/32* | (2006.01) |
| *A61B 90/30* | (2016.01) |
| A61B 17/3207 | (2006.01) |
| A61B 17/00 | (2006.01) |
| A61B 17/29 | (2006.01) |

(52) U.S. Cl.
CPC ...... *A61B 17/320016* (2013.01); *A61B 90/30* (2016.02); *A61B 17/320725* (2013.01); *A61B 2017/00367* (2013.01); *A61B 2017/00907* (2013.01); *A61B 2017/2902* (2013.01);
(Continued)

(58) Field of Classification Search
CPC .... A61B 17/320016; A61B 17/320725; A61B 2090/309; A61B 90/30; A61B 2017/00367; A61B 2017/00907; A61B 2017/2902; A61B 2017/2927; A61B 2017/320044

See application file for complete search history.

(56) References Cited

U.S. PATENT DOCUMENTS

| | | | |
|---|---|---|---|
| 3,495,586 A | | 2/1970 | Regenbogen |
| 4,608,965 A | * | 9/1986 | Anspach, Jr ....... A61B 17/0281 |
| | | | 600/101 |

(Continued)

FOREIGN PATENT DOCUMENTS

| | | |
|---|---|---|
| EP | 1440705 | 7/2004 |
| JP | 08-317928 | 12/1996 |

(Continued)

*Primary Examiner* — Anh T Dang
(74) *Attorney, Agent, or Firm* — Levine Bagade Han LLP

(57) ABSTRACT

A system for tissue dissection and retraction is disclosed herein. A tissue dissection assembly generally comprises an elongate body shaft, an actuation member movable relative to the elongate body shaft, and at least one dissector arm member having at least a first end attached to the elongate body shaft, wherein the at least one dissector arm member is adapted to reconfigure within a plane from a low profile to an expanded profile when urged via the actuation member, and wherein the at least one dissector arm is further adapted to dissect tissue within the plane. In use, the assembly dissects tissue within the plane typically by advancing the elongate body shaft into the tissue region where the dissector arm member or members are then reconfigured within the plane from its low profile to its expanded profile to thereby dissect the tissue region along the plane.

15 Claims, 19 Drawing Sheets

Related U.S. Application Data continuation of application No. 11/174,253, filed on Jul. 1, 2005, now Pat. No. 8,007,508.

(52) U.S. Cl.
CPC ............ *A61B 2017/2927* (2013.01); *A61B 2017/320044* (2013.01); *A61B 2090/309* (2016.02)

(56) References Cited

U.S. PATENT DOCUMENTS

| | | | |
|---|---|---|---|
| 4,660,571 A | 4/1987 | Hess et al. | |
| 5,195,505 A | 3/1993 | Josefsen | |
| 5,197,971 A | 3/1993 | Bonutti | |
| 5,245,987 A | 9/1993 | Redmond et al. | |
| 5,275,610 A | 1/1994 | Eberbach | |
| 5,325,848 A | 7/1994 | Adams et al. | |
| 5,339,803 A | 8/1994 | Mayzels et al. | |
| 5,345,927 A * | 9/1994 | Bonutti | A61B 17/0218 600/204 |
| 5,358,496 A | 10/1994 | Ortiz et al. | |
| 5,441,044 A | 8/1995 | Tovey et al. | |
| 5,522,839 A | 6/1996 | Pilling | |
| 5,549,625 A | 8/1996 | Bircoll | |
| 5,554,101 A | 9/1996 | Matula et al. | |
| 5,634,883 A | 6/1997 | Chin et al. | |
| 5,653,722 A | 8/1997 | Kieturakis | |
| 5,653,726 A | 8/1997 | Kieturakis | |
| 5,656,012 A | 8/1997 | Sienkiewicz | |
| 5,658,307 A | 8/1997 | Exconde | |
| 5,755,661 A | 5/1998 | Schwartzman | |
| 5,803,902 A | 9/1998 | Sienkiewicz et al. | |
| 5,860,987 A | 1/1999 | Ratcliff et al. | |
| 5,885,278 A * | 3/1999 | Fleischman | A61B 18/1492 600/374 |
| 5,888,196 A | 3/1999 | Bonutti | |
| 5,957,900 A | 9/1999 | Ouchi | |
| 6,146,401 A | 11/2000 | Yoon et al. | |
| 6,203,559 B1 | 3/2001 | Davis et al. | |
| 6,217,548 B1 | 4/2001 | Tsugita et al. | |
| 6,264,670 B1 | 7/2001 | Chin | |
| 6,277,136 B1 | 8/2001 | Bonutti | |
| 6,364,887 B1 | 4/2002 | Dworschak et al. | |
| 6,451,042 B1 | 9/2002 | Bonutti | |
| 6,468,205 B1 | 10/2002 | Mollenauer et al. | |
| 6,491,672 B2 | 12/2002 | Slepian et al. | |
| 6,506,178 B1 | 1/2003 | Schubart et al. | |
| 6,689,084 B2 | 2/2004 | Kaganov et al. | |
| 6,746,465 B2 | 6/2004 | Diederich et al. | |
| 6,764,497 B2 | 7/2004 | Fogarty et al. | |
| 6,805,692 B2 | 10/2004 | Muni et al. | |
| 6,860,892 B1 | 3/2005 | Tanaka et al. | |
| 6,866,676 B2 | 3/2005 | Kieturakis et al. | |
| 6,939,349 B2 | 9/2005 | Fleischman et al. | |
| 6,989,028 B2 | 1/2006 | Lashinski et al. | |
| 7,037,321 B2 | 5/2006 | Sachdeva et al. | |
| 7,056,329 B2 | 6/2006 | Kerr | |
| 7,118,585 B2 | 10/2006 | Addis | |
| 8,007,508 B2 | 8/2011 | Cox | |
| 2001/0016754 A1 | 8/2001 | Adams et al. | |
| 2001/0018555 A1 | 8/2001 | Raspaldo et al. | |
| 2002/0069884 A1 * | 6/2002 | Boyd | A61B 17/00234 128/898 |
| 2002/0072768 A1 | 6/2002 | Ginn | |
| 2002/0165570 A1 | 11/2002 | Mollenauer et al. | |
| 2003/0018352 A1 | 1/2003 | Mollenauer et al. | |
| 2004/0225194 A1 | 11/2004 | Smith et al. | |
| 2004/0236186 A1 | 11/2004 | Chu | |
| 2004/0236363 A1 | 11/2004 | Kieturakis et al. | |
| 2005/0080435 A1 | 4/2005 | Smith et al. | |
| 2006/0004286 A1 | 1/2006 | Chang et al. | |
| 2006/0210605 A1 | 9/2006 | Chang et al. | |
| 2006/0270910 A1 * | 11/2006 | Davis | A61B 17/0218 600/210 |
| 2007/0005093 A1 | 1/2007 | Cox | |
| 2007/0135789 A1 | 6/2007 | Chang et al. | |
| 2011/0313247 A1 | 12/2011 | Cox | |

FOREIGN PATENT DOCUMENTS

| | | |
|---|---|---|
| JP | 10-118087 | 5/1998 |
| JP | 10-509338 | 9/1998 |
| JP | 2002-345832 | 12/2002 |
| JP | 3519435 | 4/2004 |
| JP | 2005-279010 | 10/2005 |
| JP | 2006-102230 | 4/2006 |
| WO | WO 1996/010961 | 4/1996 |
| WO | WO 2004/037097 | 5/2004 |
| WO | WO 2007/005535 | 1/2007 |

* cited by examiner

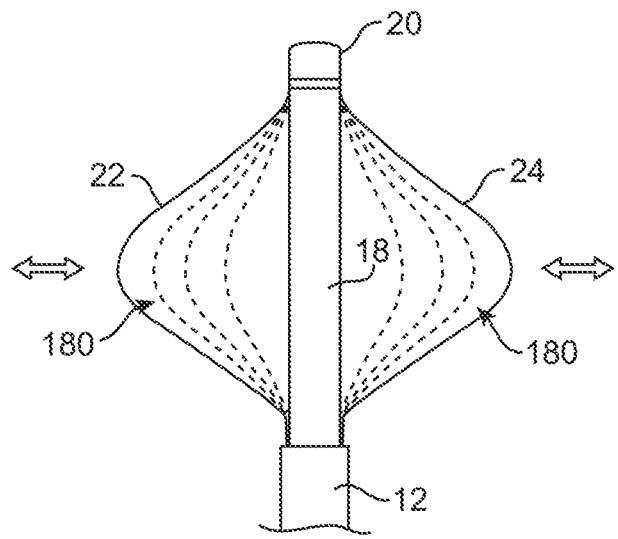
FIG. 8A
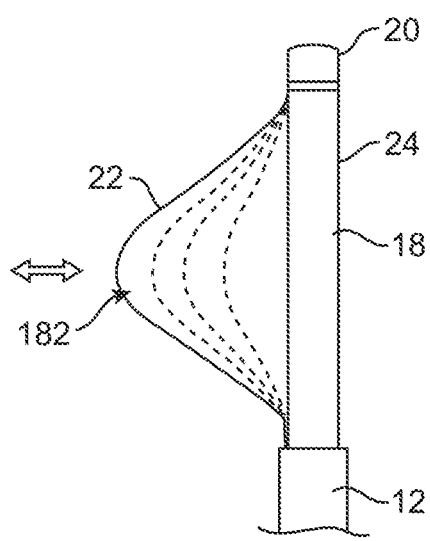 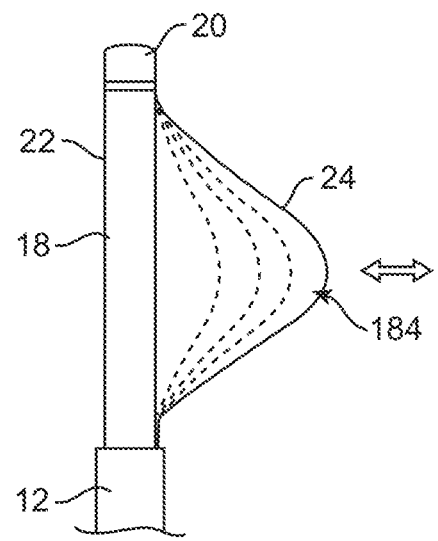
FIG. 8B            FIG. 8C

SYSTEM FOR TISSUE DISSECTION AND RETRACTION

CROSS-REFERENCE TO RELATED APPLICATIONS

This application is a continuation of U.S. patent application Ser. No. 13/220,461 filed Aug. 29, 2011 (now U.S. Pat. No. 9,168,053) which is a continuation of U.S. patent application Ser. No. 11/174,253 filed Jul. 1, 2005 (now U.S. Pat. No. 8,007,508), each of which is incorporated herein by reference in its entirety.

FIELD OF THE INVENTION

The present invention relates to systems for dissecting and/or retracting tissue. More particularly, the present invention relates to apparatus and methods for dissecting layers of tissue as well as retracting tissue regions and organs.

BACKGROUND OF THE INVENTION

Conventional instruments and methods for obtaining access to regions within the body by dissecting tissue and retracting tissue and organs have been previously accomplished through various mechanical methods. Previous devices have included expandable tissue dissectors and retractors used for dissecting or moving sub-surface tissue in arthroscopic and endoscopic surgery percutaneously introduced into a patient through small incisions made in the skin.

Many of these devices are configured to simply expand from a low profile into an expanded profile to simply provide a surface, whether by an expanded structure or via a sheath or covering, for retracting tissue regions within the body. Other devices are also expandable into an expanded profile to not only provide a retraction surface but also to dissect sub-surface regions of tissue. In either case, these devices are typically configured to mechanically expand in a number of different planes while other devices are configured to expand within a single plane. Most of these tools are mechanically expandable in a number of different configurations, for example, expandable mechanical trusses, pivoting interleaved configurations, projecting loops, etc.

Still other devices have utilized expandable balloons which are inflated within the patient through various methods. Generally, expansion is accomplished by inflating the balloon with a fluid or a gas, e.g., carbon dioxide, water, saline, etc., until the balloon is sufficiently expanded. Such balloons have also been utilized for retraction of organs and tissue regions once expanded. However, such balloons are typically lacking because they generally lack sufficient rigidity and cannot be controlled to conform to various sizes or shapes for precise application. Moreover, adequate retraction of tissue can only be accomplished when the balloon is fully expanded.

Accordingly, there is a need for instruments which are sufficiently minimally invasive for passage into a patient and which are also sufficiently rigid and precisely controllable.

BRIEF SUMMARY OF THE INVENTION

An instrument which enables a surgeon to obtain access within a patient's body through controlled dissection between tissue layers may be advanced percutaneously through one or more incisions made in a patient's skin or through an open surgical procedure.

Such a tissue dissection assembly may generally comprise an elongate body shaft, an actuation member movable relative to the elongate body shaft, and at least one dissector arm member having at least a first end attached to the elongate body shaft, wherein the at least one dissector arm member is adapted to reconfigure within a plane from a low profile to an expanded profile when urged via the actuation member, and wherein the at least one dissector arm is further adapted to dissect tissue within the plane.

In use, such a tissue dissection assembly for dissecting tissue within a plane or along a line may be utilized generally by advancing the elongate body shaft into a tissue region to be dissected, urging the at least one dissector arm member positioned adjacent to or within the tissue region to reconfigure within a plane from a low profile to an expanded profile by moving the actuation member relative to the elongate body shaft, and dissecting the tissue region along the plane via the at least one dissector arm member.

The tissue dissection assembly may include a number of optional features as well. For instance, although a single dissector arm member may be utilized in some variations, at least an additional dissector arm member may be utilized and positioned along the actuation shaft and the elongate body shaft on an opposing side of the dissector arm member. Dissector arm members may extend in opposing directions along a single plane into a dissecting configuration; alternatively, the arm members may be positioned such that they extend or reconfigure themselves along different planes relative to one another.

As the arm members deploy from their low profile shape, they may be locked into their expanded configuration or any intermediate configuration via a locking mechanism. Moreover, to facilitate insertion of the device through the tissue, a tapered or piercing distal tip, which may be optionally retractable, removable, or integrated as a permanent feature of the device, may also be included. When the dissector arm members are in their low profile configuration with respect to the actuation shaft, the arm members may simply lie adjacent to the actuation shaft. Alternatively, the actuation shaft may define openings along a length of the actuation shaft adjacent to their respective arm members for receiving, at least partially within, their respective dissector arm members. In yet another alternative, the actuation shaft or elongate body shaft may be formed into a member having a cross-sectional shape other than circular or tubular.

Actuation and locking of the arm members may be accomplished in a number of different ways. For instance, a handle assembly coupled to a proximal end of the actuation and/or elongate body shaft may be configured to advance and retract the arm members in a ratcheting manner to maintain one or more intermediate configurations of the arm members during expansion.

In another variation, the elongate body shaft may include a shaft distal portion which is configured to pivot at an angle relative to a longitudinal axis of the elongate shaft. The pivoting end effector may be angled anywhere from 0 degrees to under 180 degrees to facilitate access and deployment within the patient body.

The dissector arm members themselves may be configured into various cross-sectional geometries. Additionally, any of the dissector arm members may be coated or covered with a compliant material to alter the frictional properties of the dissector arm surfaces with respect to the tissue.

In yet another variation of the tissue dissector assembly, a pump may be fluidly connected to the assembly to provide for insufflation/exsufflation of a gas or fluid (e.g., air, carbon dioxide, saline, water, etc.) directly through the elongate body. This gas or fluid may be used before, during, or after mechanical dissection to alternatively initiate, enhance, or support dissection or to maintain or expand a dissected space. Yet another variation may include a viewing or imaging port at a distal end of the assembly or alternatively along the elongate body or even through one or more of the dissector arm members to provide for direct visualization during insertion into the tissue and during dissection.

In another variation, a light source may be provided through the assembly directly. In yet another variation, an optional covering or membrane may be disposed over the dissector arms to form a surface which expands and retracts along with the arms. Tissue retraction may be performed without the covering or membrane at all and with the dissector arms in any number of expanded configurations, i.e., fully or any number of intermediate expanded configurations.

BRIEF DESCRIPTION OF THE DRAWINGS

FIG. 8A shows a side view of an expanded and various intermediate configurations where both dissector arms may be simultaneously actuated.

FIGS. 8B and 8C show side views of alternative expanded and various intermediate configurations where either dissector arm may be actuated singularly.

DETAILED DESCRIPTION OF THE INVENTION

Figure 1A:
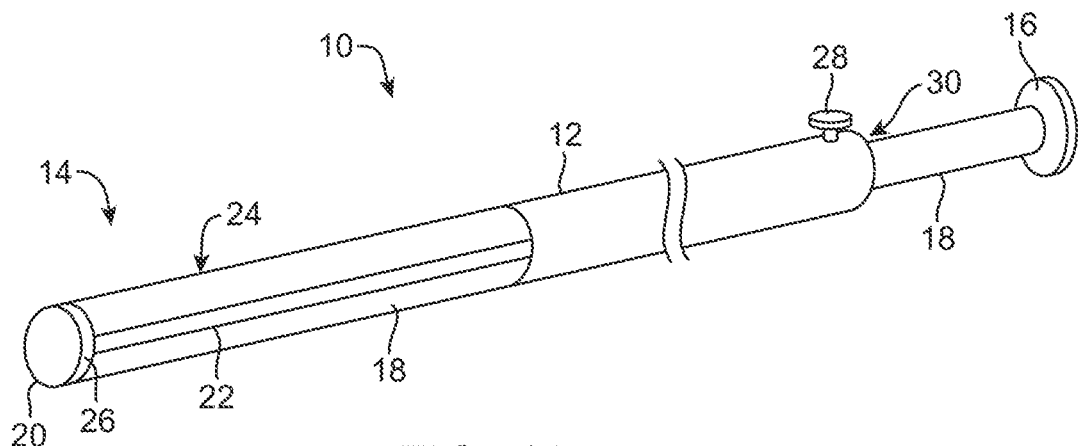
FIGS. 1A and 1B show perspective views of one variation of the tissue dissector and/or retractor in a low-profile configuration and an expanded configuration, respectively.

Dissection of tissue and tissue layers may be accomplished percutaneously through one or more incisions made in a patient's skin or through an open surgical procedure. An instrument which enables a surgeon to obtain access within a patient's body through controlled dissection between tissue layers within a plane or along a line is shown in the perspective view of FIG. 1A, which shows one example of a tissue dissector assembly 10 in a low profile configuration for insertion into the tissue region of interest. FIG. 1B shows tissue dissector assembly 10 in a fully expanded tissue dissection configuration.

Such a variation of tissue dissector assembly 10 may generally comprise an elongate body shaft 12 appropriately sized, e.g., similarly to a conventional surgical or laparoscopic instrument, having a tissue dissector end effector 14 located at a distal end of elongate body shaft 12. Handle 16 may be coupled proximally of body shaft 12 for manipulating an actuation shaft 18 and an atraumatic tip 20 may be attached at a distal end of assembly 10 to facilitate its insertion into the tissue region to be dissected within the patient. Actuation shaft 18 may comprise an elongate member configured to be slidably positioned through a lumen of body shaft 12.

At least a first end of a single dissector arm member 22 may be attached at arm member attachment 26 to a distal end of actuation shaft 18 and a second end may be attached to a distal end of elongate body shaft 12. Although actuation shaft 18 is shown in the figures as extending entirely through body shaft 12 through body shaft lumen 30, actuation shaft 18 may extend at least partially through, over, or alongside body shaft 12 in other variations of the assembly 10. Moreover, in other variations, a secondary shaft may be coupled to a proximal end of actuation shaft 18 such that the secondary shaft extends proximally to handle 16.

Although a single dissector arm member 22 may be utilized in some variations, at least an additional dissector arm member 24 may be utilized and positioned as shown along actuation shaft 18 and elongate body shaft 12 on an opposing side of dissector arm member 22. Dissector arm members 22, 24 may be positioned along assembly 10, e.g., at 180 degrees with respect to one another, so that when they are actuated to deploy, arm members 22, 24 may extend in opposing directions along a single plane into a dissecting configuration, as shown in FIG. 1B. Alternatively, arm members 22, 24 may be positioned such that they extend or reconfigure themselves along different planes, as further described below.

Each of the arm members 22, 24 may be fabricated from a biocompatible material such as flexible or compliant metal, e.g., spring stainless steel or a superelastic or shape memory alloy such as Nitinol, so that once arm members 22, 24 have been reconfigured from their low profile shape to their expanded shape, the arms may collapse back into their low profile. Alternatively, arm members 22, 24 may be fabricated from inflexible or partially flexible metals or polymers which are connected via one or more hinges, e.g., pivoted hinges or living hinges, etc., along the length of arm members 22, 24 to enable reconfiguration of arm members 22, 24. In yet another alternative, arm members 22, 24 may be fabricated from any number of flexible polymeric materials, e.g., polycarbonate, polyethylene, polyamide, etc. Moreover, these flexible polymeric arm members 22, 24 may be optionally fabricated to be translucent such that tissue being dissected and/or retracted may be visualized directly through the translucent arm members 22, 24 from within the patient body utilizing any number of imagers, as further described below.

Figure 1B:
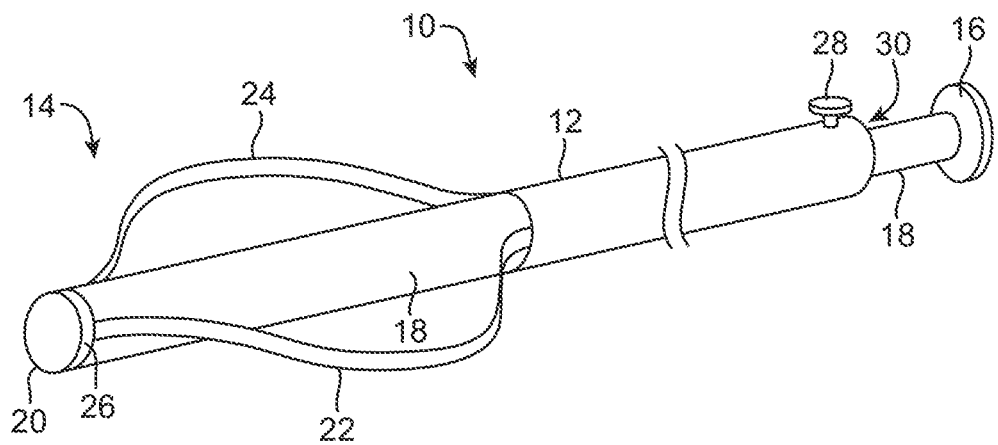

As arm members 22, 24 deploy from their low profile shape, as shown in FIG. 1A, they may locked into their expanded configuration, as shown in FIG. 1B, or any intermediate configuration via locking mechanism 28, which may be located along elongate body shaft 12, actuation shaft 18, or handle 16. To release the locked configuration of arm members 22, 24, locking mechanism 28 may be re-depressed. Locking mechanism 28 is shown as a push-button mechanism, however, any number of conventional locking mechanisms for maintaining, the relative position of actuation shaft 18 with respect to elongate body shaft 12 may be utilized, e.g., friction locks, ratcheting mechanisms (as shown below), pin locks, etc.

Figure 2A:
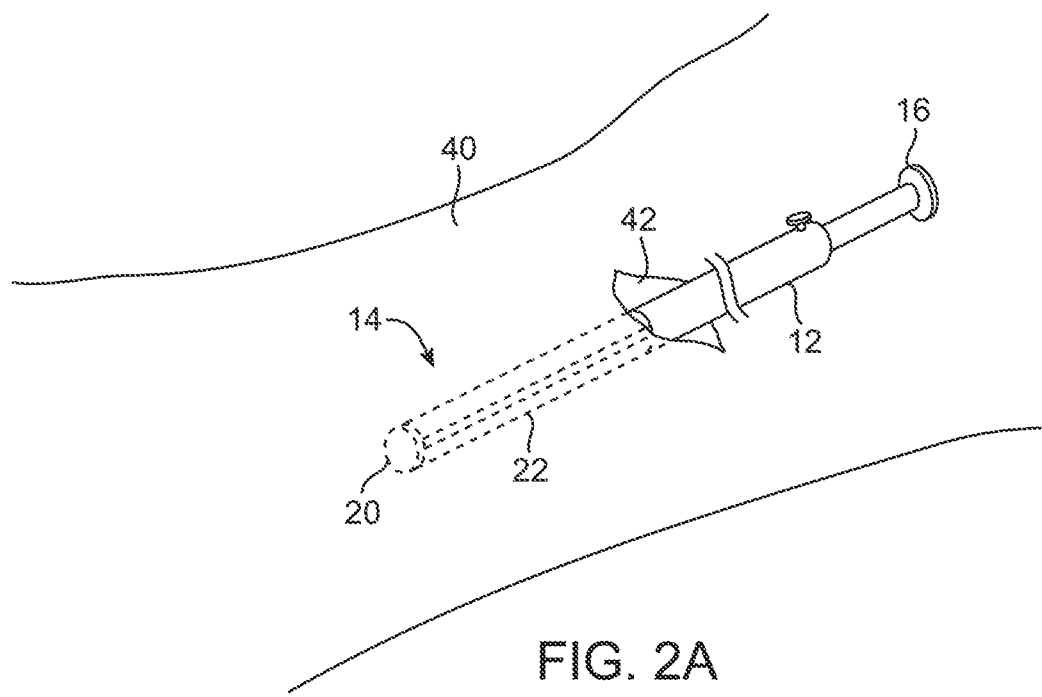
FIGS. 2A and 2B show one example for percutaneously introducing the device of FIGS. 1A and 1B into a patient, e.g., to dissect layers of tissue within the abdominal wall.
Figure 2B:
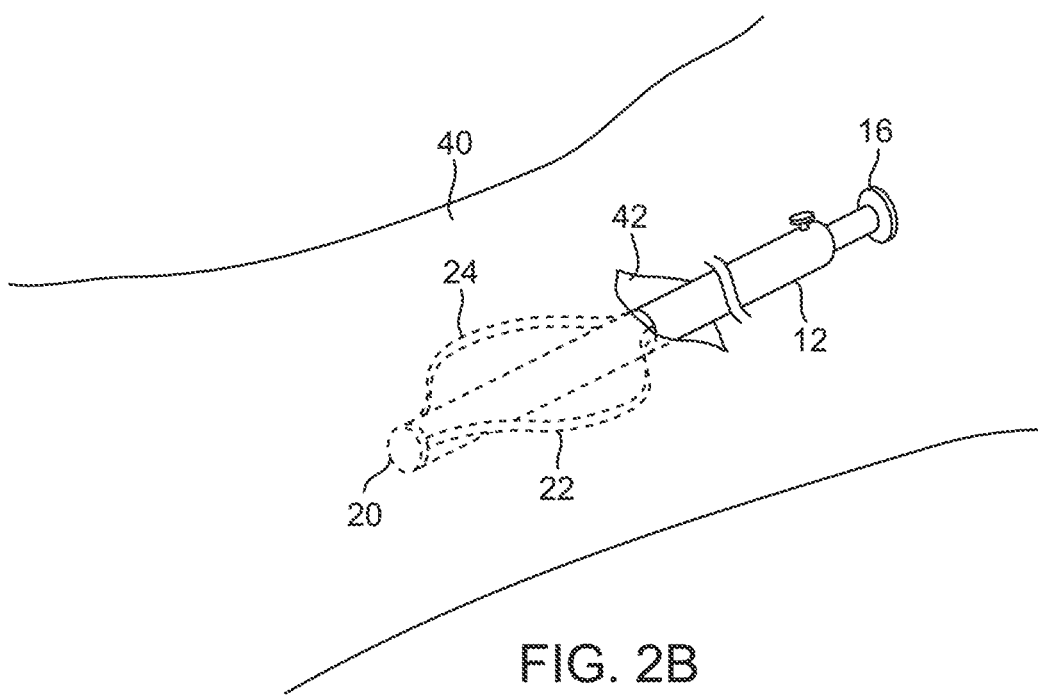

In use, one method may generally comprise inserting the assembly 10 into a patient body 40 through an incision 42, e.g., through a patient's umbilicus and into the abdominal wall as shown in FIG. 2A, with arm members 22, 24 in their low profile configuration. The atraumatic tip 20 of the device may prevent unnecessary trauma to the surrounding tissue as the device is inserted blindly, under direct vision, or through a separate videoscope. In other variations, a videoscope or imager may be integrated or included within the device, as described below in further detail. In either case, the device may be pushed, e.g., towards the pubic bone, while maintaining a presence within a desired tissue plane. Once the tissue plane is to be dissected, handle 16 may be advanced with respect to elongate body shaft 12 such that arm member 22, 24 are expanded to thereby dissect the surrounding tissue along the desired tissue plane, as shown in FIG. 2B.

Figure 2C:
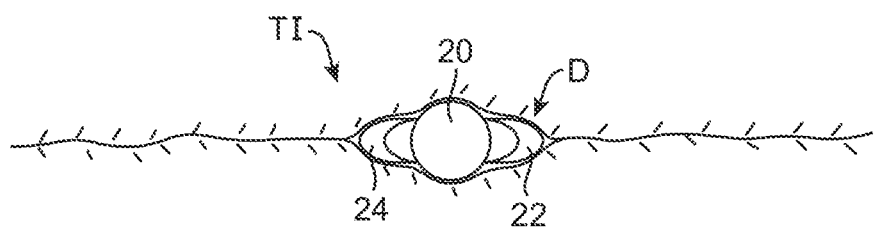
FIGS. 2C to 2E show the device of FIGS. 2A and 2B expanded and subsequently retracted within the patient body to dissect the tissue region of interest.
Figure 2D:
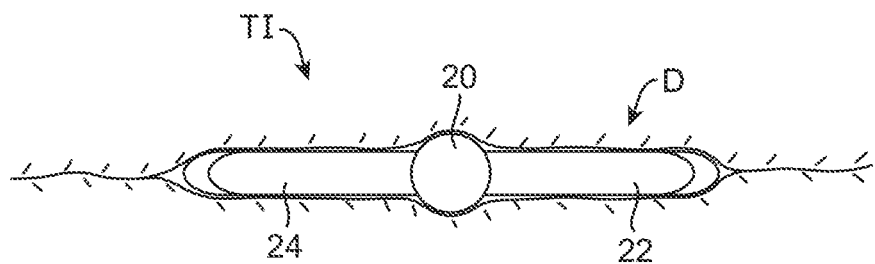
Figure 2E:
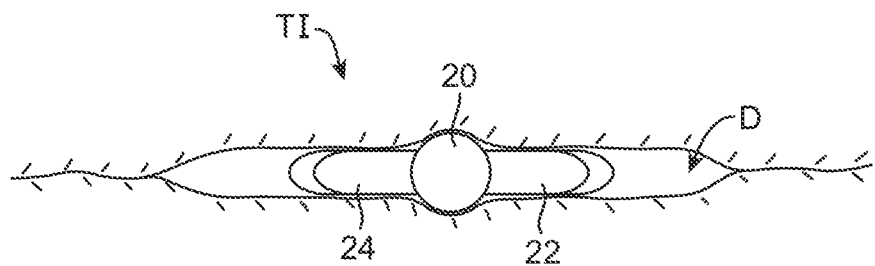

FIGS. 2C to 2E show end views of an example of the tissue dissection assembly 10 during a tissue dissection procedure. As previously described, the device may be inserted into the tissue region of interest TI between adjacent tissue planes with arm member 22, 24 in their low profile shape, as shown in FIG. 2C. Arm member 22, 24 may then be expanded, either fully or to an intermediate position, to thereby dissect the surrounding tissue TI from one another, as shown in FIG. 2D. Expansion of arm member 22, 24 may be continued or retracted to thereby leave an open region D between adjacent tissue layers, as shown in FIG. 2E.

The arm member 22, 24 may also be deployed and retracted as many times as necessary until the desired degree of tissue separation or dissection has occurred. Additionally, the device may be applied in a sweeping motion, e.g., left-to-right, or rotated about its longitudinal axis by any number of degrees until the tissue planes have been appropriately separated. Moreover, insufflation of a gas or fluid may optionally be utilized through a separate instrument or through the assembly itself to further aid tissue dissection, as described below in further detail.

Aside from use for dissection of tissue surrounding the peritoneal space, the assembly may be utilized in a number of different regions throughout the body. For example, the device may be inserted into the body for providing access to the kidneys in the extra-peritoneal space, to the prostate in the pre-peritoneal space, or for providing vascular access. The assembly may also be utilized for providing access to regions in the legs, arms, etc., as so desired.

Figure 3A:
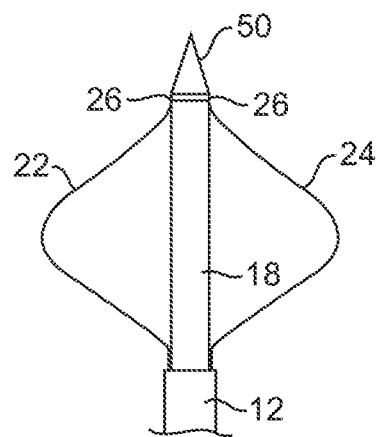
FIG. 3A shows an example of one configuration for the dissector having a tapered end for facilitating insertion into the patient body and between tissue layers.
Figure 3B:
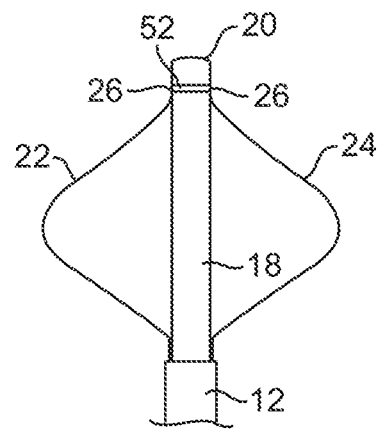
FIG. 3B shows another example of a configuration having a blunted atraumatic tip and non-pivoting, expandable dissector arms.
Figure 3C:
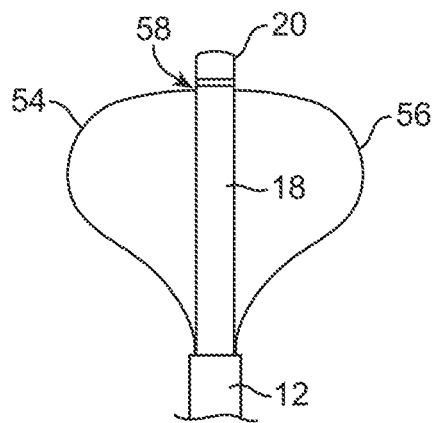
FIG. 3C shows another example of a configuration having a blunted atraumatic tip but with dissector arms which are pivotable relative to the elongate shaft.

To facilitate insertion of the device through the tissue, a tapered or piercing distal tip 50 may be included, as shown in FIG. 3A. This piercing distal tip 50 may be optionally retractable, removable, or integrated as a permanent feature of the device. The dissector arm members may be configured to expand from a low profile into an expanded profile having any number of expanded configurations. For instance, as mentioned above, the distal ends of dissector arms 22, 24 may be attached to the distal end or portion of actuation shaft 18 via a securement member 52, e.g., band, ring, etc., as shown in FIG. 3B, or the arms 22, 24 may be simply attached directly into receiving channels or via an adhesive in other variations. Allowing for such a non-pivoting attachment may allow for arm members 22, 24 to conform into a symmetrically arcuate or curved configuration. Alternatively, the dissector arms may be pivotably connected via a pivot or pinned connection 58 which may allow for arm members 54, 56 to conform into an asymmetric curve, as shown in FIG. 3C.

In yet another alternative, arm members 60, 62 may be connected via pivot or pinned connection 64 while actuation shaft 18 is overdriven with respect to elongate body shaft 12.

Figure 3D:
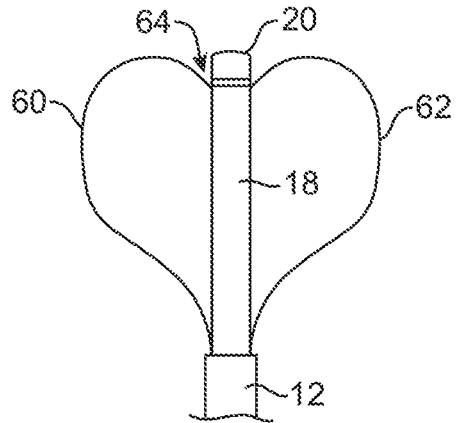
FIG. 3D shows another example having dissector arms which are configured to be driven into an over-expanded configuration.
Figure 3E:
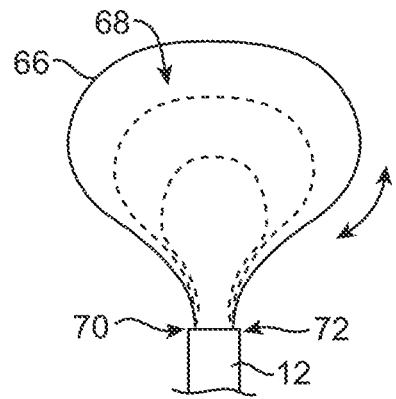
FIG. 3E shows yet another example of a single dissector arm expandable into a looped configuration.

Overdriving actuation shaft 18 may conform arm members 60, 62 into an overextended arcuate configuration, as shown in FIG. 3D. In another variation, a single dissector arm 66 may be utilized to form a single looped configuration, as shown in FIG. 3E. A first end of looped arm 66 may be connected at a fixed attachment point 70 and a second end of looped arm 66 may be connected at a fixed attachment point 72 to an actuation shaft which is translatably disposed with respect to elongate body shaft 12. Translation of the actuation shaft relative to elongate body shaft 12 may deploy looped arm 66 from its low profile configuration into its fully deployed configuration, or into any number of intermediate positions or configurations by moving a single side of dissector arm 66 in the direction of the arrow shown in FIG. 3E.

Figure 3F:
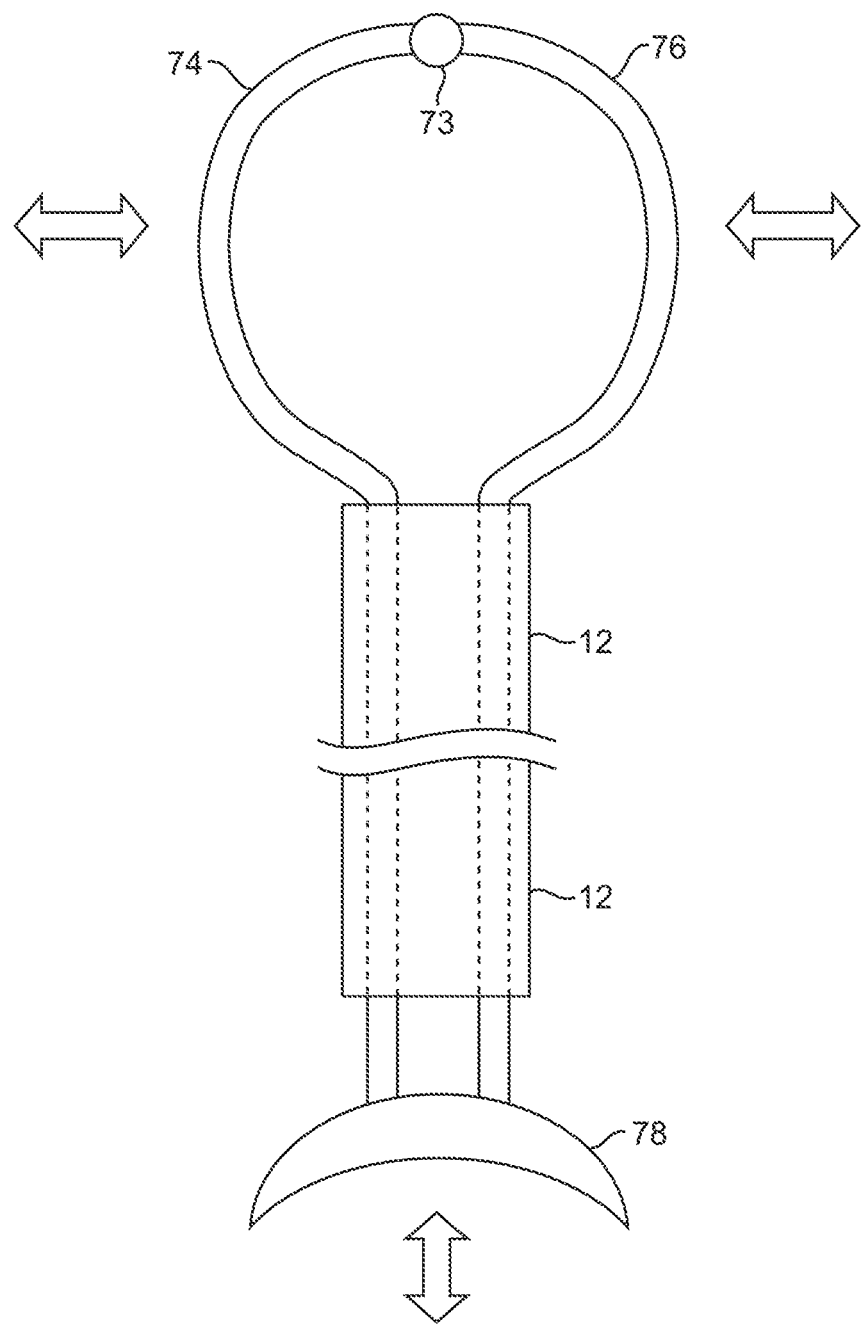
FIG. 3F shows another variation where each dissector arm member may be directly connected to a handle such that an actuation shaft may be omitted entirely.

Turning to FIG. 3F, an example of an instrument similar to that shown in FIG. 3E is shown. A single looped dissector arm may be employed, but in this variation, two separate dissector arms 74, 76 are illustrated rotatingly joined via rotating attachment 73. Each of the dissector arms 74, 76 may extend entirely through shaft 12 and attach directly to a handle 78, which may be urged distally and proximally in the directions shown to expand or retract dissector arms 74, 76, as shown by their respective arrows. In this variation, because the proximal ends of dissector arms 74, 76 are attached directly to the handle, an actuation shaft may be omitted entirely. Other features, e.g., locking mechanisms or ratcheting mechanisms described herein, may be integrated in combination with this embodiment, as so desired.

Figure 4A:
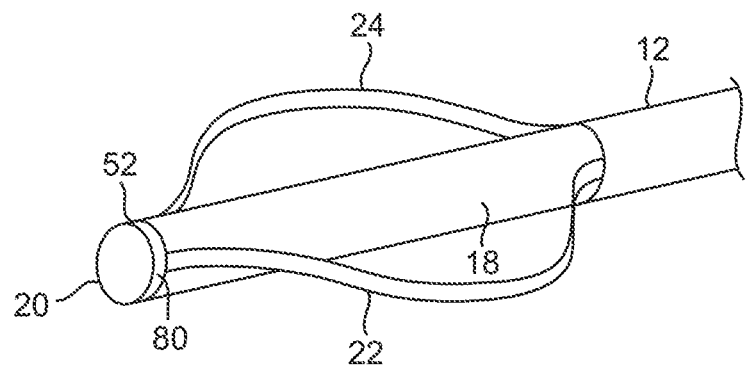
FIG. 4A shows a detailed perspective view of a variation having non-pivoting expandable dissector arms.

In alternative variations, each of the dissector arm members may attached in alternating methods. For instance, in the example of FIG. 4A, a first dissector arm 22 may be connected via a pivoting attachment 80 while the second arm dissector arm 24 may be attached to securement member 52 via a non-pivoting attachment such that each arm 22, 24 conforms to a different configuration. In yet another alternative shown in FIG. 4B, each of the distal ends of the dissector arm members 22, 24 may comprise a looped connector 84 which slides along a looped attachment member 82 positioned at the distal end of actuation shaft 18. When actuation shaft 18 is thus actuated, each of the dissector arm members 22, 24 may slidingly rotate about looped attachment member 82 in a non-pivoting manner to expand the arm members 22, 24.

Figure 4B:
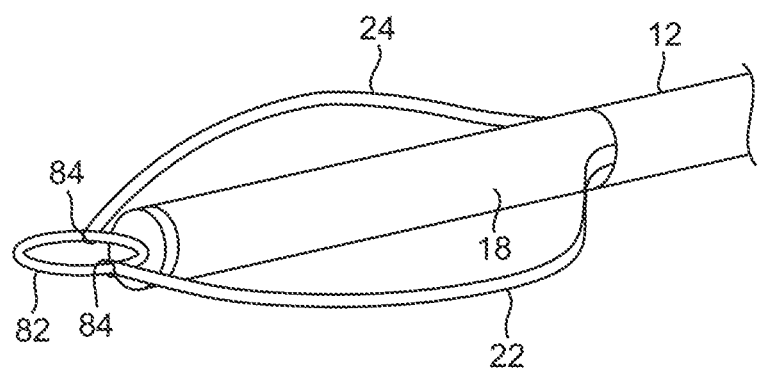
FIGS. 4B and 4C show detailed perspective and top views of another variation having reconfigurable dissector arms slidable over a ring or curved support member.
Figure 4C:
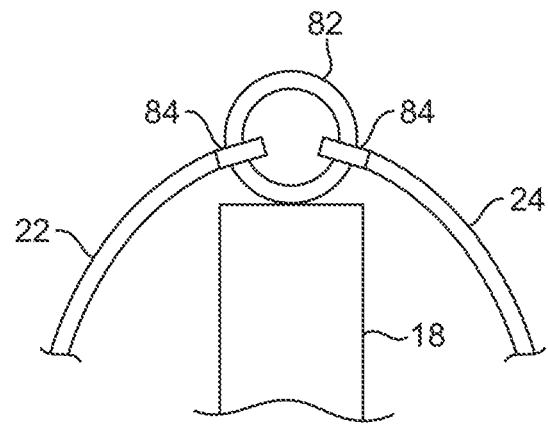
Figure 4D:
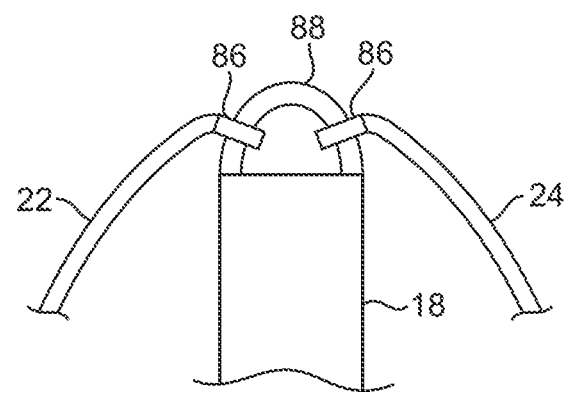
FIG. 4D shows another variation having a semi-circular support member.

FIG. 4C shows a detailed side view of the looped attachment of FIG. 4B. As illustrated, looped attachment member 82 may be formed as a circular ring attached to a distal end of actuation shaft 18. Looped connectors 84 at the distal ends of dissector arm members 22, 24 may slide along looped attachment member 82. Although the looped attachment member 82 is shown in this variation as a circular member, other configurations may be utilized, as practicable. For instance, FIG. 4D shows a semi-circular attachment member 88 over which angled connectors 86 located at the distal ends of dissector arm members 22, 24 may slide over or upon. Other shapes for attachment members may also include elliptical, angled, straight, triangular, etc.

Figure 5A:
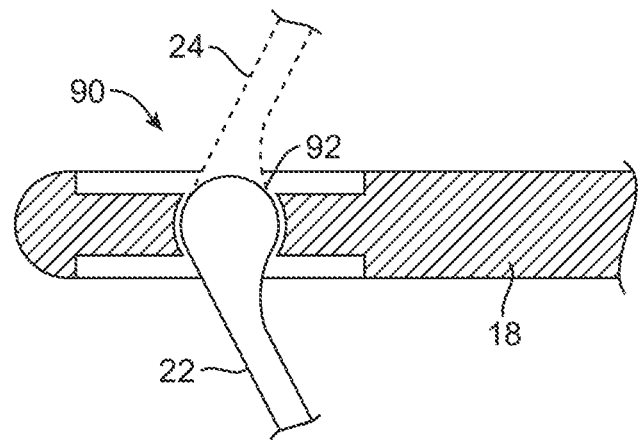
FIG. 5A shows a partial cross-sectional top view of interleaved dissector arms held within the elongate support member such that the dissector arms are rotatable relative to one another over contacting bearing surfaces.
Figure 5B:
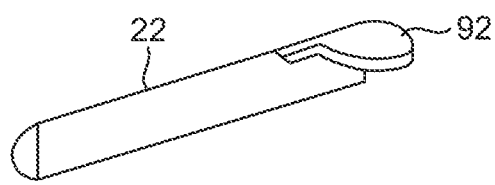
FIG. 5B shows a partial perspective view of one of the dissector arms illustrating the bearing surface.

Another variation for arm member connection is shown in the detail partial cross-sectional top view in FIG. 5A of actuation shaft 18 and rotational connection 90 of the interleaved distal ends of arm members 22, 24. As illustrated in the partial perspective view of FIG. 5B, the distal ends of arm members 22, 24 may be formed into an interleaved element or member 92 which together form a complementary and rotational connection, as shown in FIG. 5A. When the two arm members 22, 24 are interleaved with one another, they may be securely held within actuation shaft 18 while also allowing for free rotation with respect to one another without the need for a pivot joint or connection.

Figure 5C:
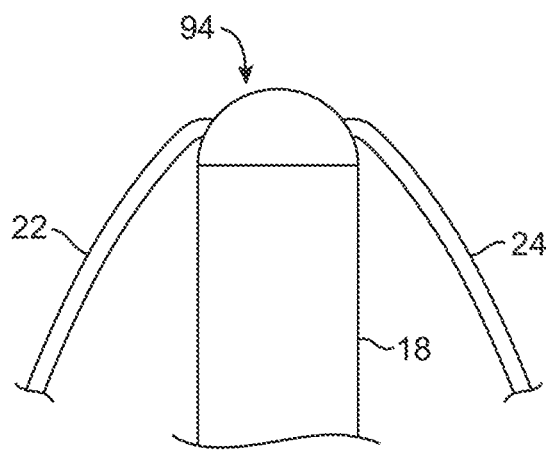
FIGS. 5C and 5D show top and side views, respectively, of another variation in which the distal ends of the dissector arm members may be keyed to traverse through respective slots or grooves defined within a housing member.
Figure 5D:
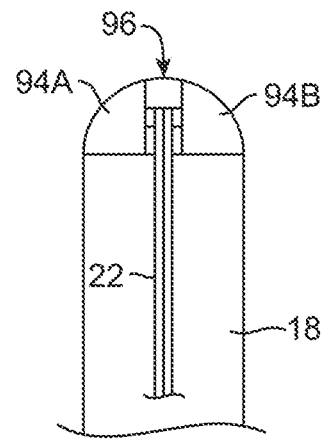
Figure 5E:
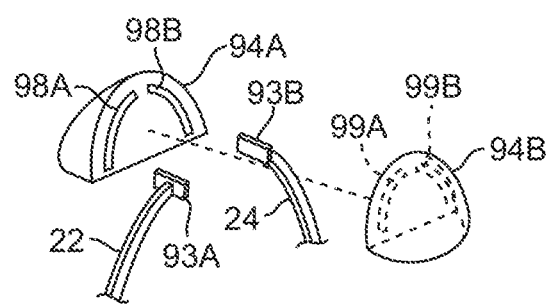
FIG. 5E shows an exploded assembly view of the housing member of FIGS. 5C and 5D.

Yet another variation for arm member connection is shown in FIGS. 5C to 5E, which shows a keyed connection for the arm members. As seen in FIG. 5C, a keyed attachment housing 94 may be disposed at a distal end of actuation shaft 18 and have distal ends of dissector arm members 22, 24 slidingly connected within housing 94. FIG. 5D shows a side view of attachment housing 94, which, in one variation, may be comprised of individual corresponding half members 94A, 94B which may be connected to one another and/or to actuation shaft 18 in a corresponding complementary attachment. Members 94A, 94B connected to actuation shaft 18 may define a slot 96 between the corresponding members 94A, 94B through which the dissector arm members 22, 24 may traverse when expanding or retracting.

FIG. 5E shows an exploded assembly view of the attachment housing members 94A, 94B and the keyed distal ends 93A, 93B of their respective dissector arm members 22, 24. Keyed channels, slots, or grooves 98A, 98B may be defined within attachment housing member 94A while corresponding channels, slots, or grooves 99A, 99B may be likewise defined within attachment housing member 94B. When attachment housing members 94A, 94B are correspondingly positioned relative to one another, each of the slots 98A, 98B may face in apposition to their respective slots 99A, 99B such that the distal end of dissector arm member 22 having a bearing or sliding member 93A may be keyed to traverse within the apposed slots 98A and 99A. Likewise, the distal end of dissector arm member 24, also having a corresponding bearing or sliding member 93B, may be keyed to traverse within the apposed slots 98B and 99B.

Each of the apposed slots 98A, 99A and 98B, 99B may be defined in a curved or arcuate path within their respective attachment housing members 94A, 94B such that when dissector arm members 22, 24 are expanded or retracted during a procedure, their bearing or sliding members 93A, 93B may freely slide securely within their respective slots.

Figure 6A:
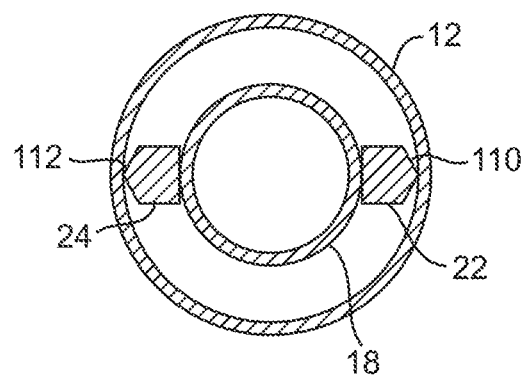
FIGS. 6A to 6C show cross-sectional end views of the dissector arm assembly in low-profile configurations illustrating various assembly configurations where the dissector arms may be profiled adjacent to the actuation shaft, partially within the actuation shaft, or having the elongate body shaft in a non-circular shape.

When the dissector arm members 22, 24 are in their low profile configuration with respect to the actuation shaft 18, the arm members 22, 24 may simply lie adjacent to actuation shaft 18, as shown in the partial cross-sectional end view of FIG. 6A. The arm members 22, 24, when in their low profile configuration, may have a diameter which is less than or equivalent to a diameter of elongate body shaft 12. Dissector arm members 22, 24 are shown in this example as each having a respective dissecting edge 110, 112 defined along an outer surface of each arm members 22, 24 to facilitate the dissection of tissue.

Figure 6B:
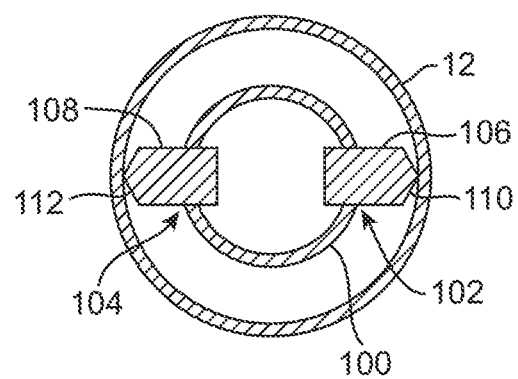

In another variation, actuation shaft 100 may define openings 102, 104 along a length of actuation shaft 100 adjacent to their respective arm members 106, 108 for receiving, at least partially within, their respective dissector arm members 106, 108, as shown in the cross-sectional end view of FIG. 6B. Arm members 106, 108 may rest at least partially within their openings 102, 104 when in their low profile for advancement into a patient body. Upon deployment to their expanded profile, arm members 106, 108 may deploy as described above.

Figure 6C:
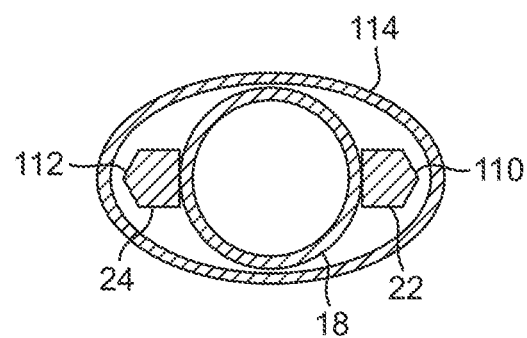

In yet another alternative, actuation shaft 18 or elongate body shaft 114 may be formed into a member having a cross-sectional shape other than circular or tubular. For example, as shown in the example of FIG. 6C, elongate body shaft 114 may be formed to have an elliptical or oval cross-section. Other cross-sectional shapes may be utilized as desired and as practicable, e.g., triagonal, square, octagonal, etc.

Figure 6D:
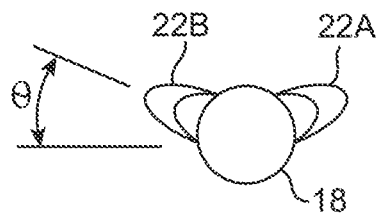
FIGS. 6D to 6F show end views of alternative variations where two or more dissector arms may be angled relative to one another.
Figure 6E:
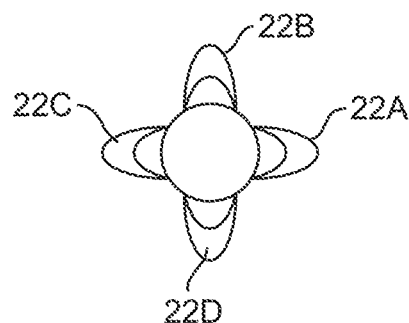
Figure 6F:
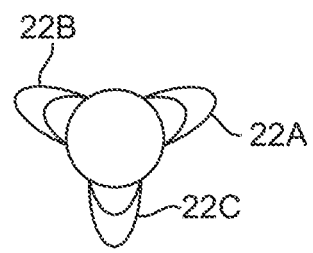

In other variations, the arm members may be angled with respect to one another such that they expand in a non-planar manner. The example shown in FIG. 6D illustrates arm members 22A, 22B each at some angle, Θ, which may be greater than 0 degrees and less than 90 degrees with respect to actuation shaft 18. In yet other variations, more than one or two arm members may be utilized, as shown in the example of FIG. 6E, which illustrates in end view four arm members 22A, 22B, 22C, 22D which may uniformly spaced about actuation shaft 18 with respect to one another. FIG. 6F shows another example utilizing three arm members 22A, 22B, 22C which may be uniformly spaced from one another about actuation shaft 18. These examples are not intended to be limiting in any way and are presented merely as examples. Other variations in number of arm members and spacing and angling between arm members are intended to be included in this disclosure.

Figure 7:
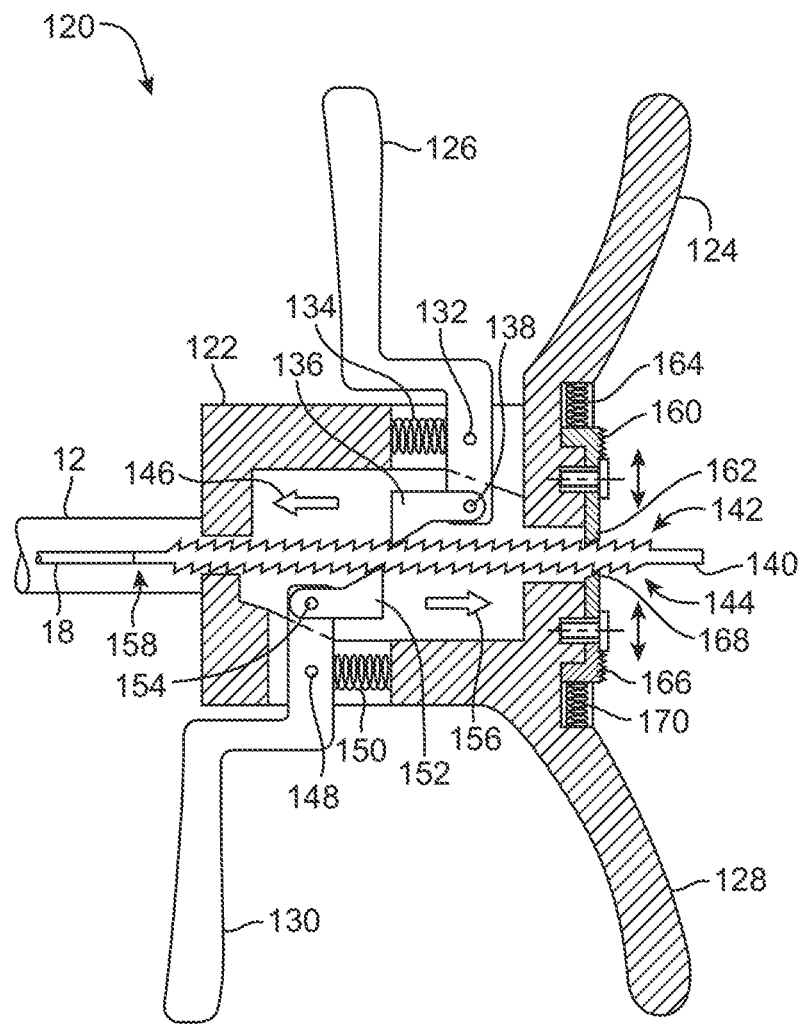
FIG. 7 illustrates a cross-sectional side view of one example for a handle assembly optionally configured to ratchet the dissector arms into any number of deployed and retracted configurations.

Actuation and locking of the arm members may be accomplished in a number of different ways. FIG. 7 shows one example of an alternative handle assembly 120 which may be utilized. Such a handle assembly 120 may be configured to advance and retract the arm members in a ratcheting manner as well as to maintain one or more intermediate configurations of the arm members during expansion. Handle assembly 120 may be coupled to a proximal end of elongate body shaft 12 and actuation shaft 18 and manipulated externally of a patient body.

Generally, handle assembly 120 may comprise housing 122 to which one or more handle members 124, 128 may be attached. Each handle member may have a respective actuation or retraction handle aligned in apposition for either advancing or retracting the actuation shaft 18 relative to elongate body shaft 12. For example, handle member 124 may have actuation handle 126 for actuating the advancement of actuation shaft 18 relative to elongate body shaft 12 to expand the arm members and handle member 128 may have retraction handle 130 in apposition therewith for actuating the retraction of actuation shaft 18 relative to elongate body shaft 12 to retract the arm members. Each of the actuation handles 126, 130 may pivot about respective pivots 132, 148 and may also include a biasing element, such as respective spring members 134, 150 for maintaining a bias in each actuation handle 126, 130. Each of the actuation handles 126, 130 may be further pivotably connected at pivots 138, 154 within housing 122 to a respective pawl member 136, 152.

Each of the pawl members 136, 152 may be biased to rest against a bi-directional rack member 140 having a first set of angled teeth or projections 142 on a first side of rack member 140 and a second set of angled teeth or projections 144 on a second side of rack member 140 where the second set of projections 144 are angled in an opposite direction to the first set of projections 142. The first set 142 may be angled in a first direction with respect to pawl 136 to advance rack 140 in a first distal direction 146 when engaged by pawl 136 to expand the arm members. Manipulation of actuation handle 126 relative to handle 124 may thus move pawl member 136 in a reciprocating manner to engage first set 142 and advance rack 140 distally with each stroke. Likewise, manipulation of actuation handle 130 relative to handle 128 may likewise move pawl member 152 in a reciprocating manner to engage second set 144 and advance rack 140 in a proximal direction 156 with each stroke. A proximal end of actuation shaft 18 may be coupled to rack 140 via connection 158. Alternatively, a proximal portion of actuation shaft 18 may be formed into a bi-directional rack.

This optional ratcheting of the arm member expansion and retraction may enable a controlled deployment of the arm members. Moreover, locking mechanisms may be incorporated in handle assembly 120 to ensure that once the arm members have been expanded to their fully deployed configuration or to any intermediate configuration, a configuration of the arm members may be set and maintained despite releasing the handles. An example for incorporating locking features may also be seen in FIG. 7 in locking member 160 having a rack engagement 162 and locking member 166 having a rack engagement 168. Locking members 160, 166 may each have a respective biasing element such as spring elements 164, 170 for engaging and locking rack member 140 during advancement and retraction to ensure that release of handles 126, 130 does not release rack member 140.

As mentioned above, dissector arm members 22, 24 may be deployed, expanded, or retracted in any number of intermediate configurations 180. Moreover, expansion and retraction of arm members 22, 24 may be accomplished simultaneously such that the arm members 22, 24 dissect the surrounding tissue on either side in a simultaneous manner, as shown in FIG. 8A. Alternatively, either arm member may be actuated and deployed independently from one another. FIG. 8B shows one example where arm member 22 may be expanded and retracted either fully or in any number of intermediate positions 182 while maintaining the other arm member 24 in its low profile position. Likewise, FIG. 8C shows another example where the other arm member 24 may be expanded and retracted also either fully or in any number of intermediate positions 184 while maintaining, the arm member 22 in its low profile position.

Figure 9A:
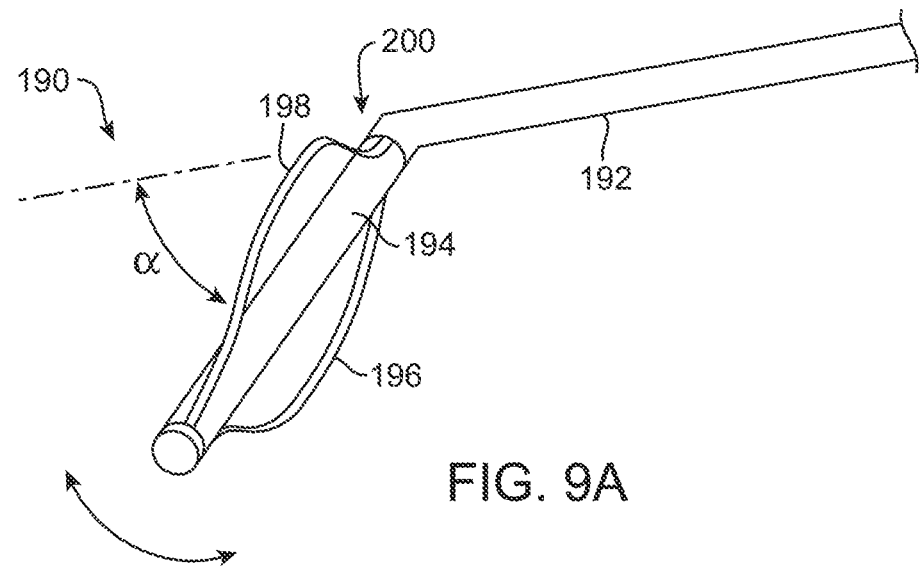
FIG. 9A shows an example of another variation where the tissue dissector end effector may be optionally pivoted via a passive or active mechanism relative to the elongate body shaft to facilitate access and use within the patient body.

Another feature which may be optionally incorporated into the assembly may include a pivoting tissue dissector end effector 190, as shown in the perspective view of FIG. 9A. In such a variation, elongate body shaft 192 may include a shaft distal portion 194 which is configured to pivot at an angle, a, relative to a longitudinal axis of elongate shaft 192. Pivoting end effector 190 may be angled anywhere from 0 degrees to under 180 degrees to facilitate access and deployment within the patient body. Even when angled, dissector arm members 196, 198 may be expanded and retracted in any number of configurations, as described above.

In pivoting end effector 190, various active or passive mechanisms may be employed. For instance, pivoting end effector 190 may be configured to self-pivot to a set predetermined angle, a, e.g., 45 degrees. In such an embodiment, a bending or pivoting portion proximal to end effector 190 may be fabricated from a spring stainless steel or shape memory alloy such as Nitinol such that when the instrument is deployed, unlocked, or otherwise unconstrained, end effector 190 automatically reconfigures to curve, angle, or curl into its predetermined deployment configuration, such as that shown in FIG. 9A.

Figure 9B:
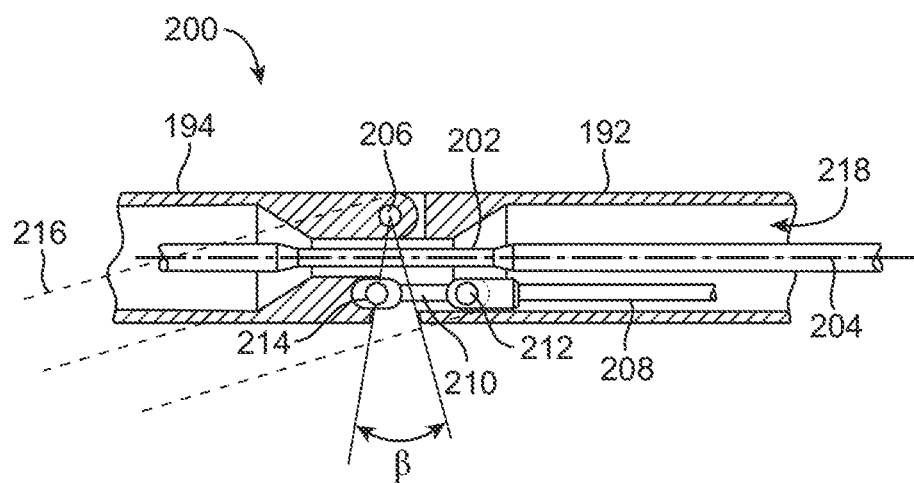
FIG. 9B shows a partial cross-sectional view of one example for pivoting the end effector assembly relative to the elongate body shaft.

FIG. 9B shows a detail partial cross-sectional view of the distal portion of elongate body shaft 192 and shaft distal portion 194 to illustrate another example for a pivoting mechanism 200. This example shows an actively actuated pivoting, bending, or curling mechanism. As shown, an actuation shaft 204 for actuating dissector arm members 196, 198 may extend through lumen 218 defined through shaft 192 and 194. A portion of actuation shaft 204 may include a bending or pivoting portion 202 which may transmit a longitudinal actuation force along the curved or angled portion 202. The pivoting portion 202 may be comprised of a reduced section of actuation shaft 204 capable of bending repeatedly or it may alternatively be comprised of a linkage to enable force transmission over a curved or angled section.

Shaft distal portion 194 may be pivotably attached to elongate body shaft 192 via dissector assembly pivot 206 to enable free rotation of shaft distal portion 194 relative to elongate body shaft 192 when actuated via pivot actuation shaft 208. The proximal end of pivot actuation shaft 208 may be routed through and/or connected to the handle assembly to allow for manipulation of shaft 208. By urging shaft 208 distally or proximally, a longitudinal force may be transmitted to actuate shaft distal portion 194, which may in turn transmit this force to pivot shaft distal portion 194 relative to elongate body shaft 192, e.g., to some angled position as illustrated by an example of displaced position 216. The angle by which distal portion 194 may pivot relative to body shaft 192 may be determined by a number of different methods, e.g., the angle, β, over which pivot 214 traverses with respect to pivot 206 when actuation shaft 208 is urged distally or proximally. Shaft 208 may be coupled to distal portion 194 via pivot linkage 210, which may in turn be pivotably coupled to distal portion 194 via pivot 214 and to actuation shaft 208 via pivot 212. The details for pivoting distal portion 194 are intended to be merely illustrative and are not intended to be limiting in any way.

Figure 10:
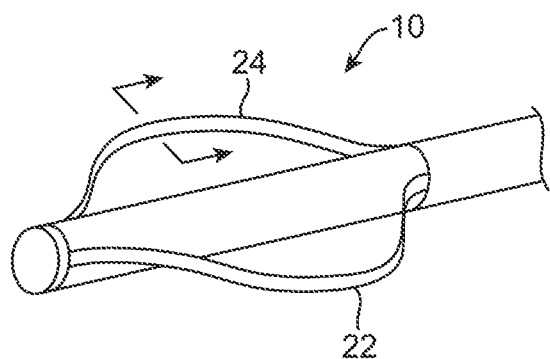
FIG. 10 illustrates an exemplary tissue dissector assembly.

Turning now to variations in dissector arm members, FIG. 10 shows an example of tissue dissector assembly 10 and dissector arm members 22, 24. FIGS. 11A to 11K show examples of some of the various cross-sections into which dissector arm members 22, 24 may be formed. These examples are intended to be illustrative of various configurations and are not intended to be limiting in any way. Other configurations for dissecting tissue which are not shown but which are obvious are intended to be included.

Figure 11A:
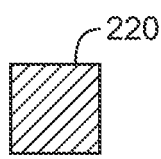
FIGS. 11A to 11K illustrate some examples for various cross-sectional profiles for the dissector arm members.
Figure 11B:
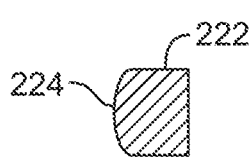
Figure 11C:
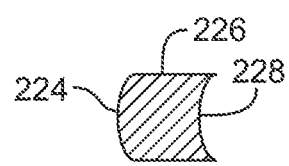
Figure 11D:
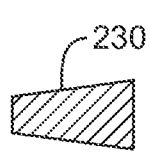
Figure 11E:
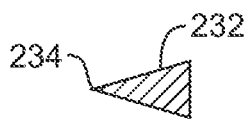
Figure 11F:
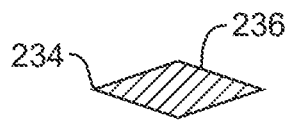
Figure 11G:
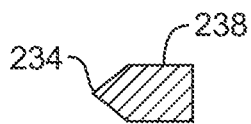
Figure 11H:
Figure 11I:
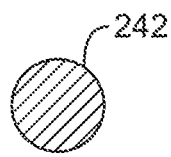
Figure 11J:
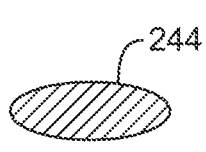
Figure 11K:
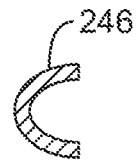

FIG. 11A shows a square cross-section 220 which may be potentially utilized although such a blunt cross-section may not be optimized for dissecting tissue. FIG. 11B shows an example in partially curved cross-section 222 having a curved outer surface 224 for contacting and dissecting the tissue. FIG. 1 IC shows another example in curved cross-section 226 which has a curved outer surface 224 and a concavely curved inner surface 228. FIG. 11D shows a tapered cross-section 230 having a partially blunted outer surface while FIG. 11E shows a tapered cross-section 232 having a cutting tip 234 for dissecting tissue. FIG. 11F shows a similarly tapered cross-section 236 having a diamond-shape. FIG. 11G shows a tissue cutting cross-section 238 having a partially rectangular portion which tapers into a cutting tip 234. FIG. 11H shows another cross-section in a tear-shaped configuration 240. FIG. 11I shows a circular cross-section 242 and FIG. 11j shows another cross-section 244 which is elliptically shaped. Finally, FIG. 11K shows a cross-section which is comprised generally of a curved outer surface and a convex inner surface configuration 246.

In addition to various cross-sectional geometries, any of the dissector arm members may be additionally coated or covered with a compliant material to alter the frictional properties of the dissector arm surfaces. For instance, they may be covered with a material, e.g., polymers, to further decrease any frictional resistance against tissue. Alternatively, the dissector arm surfaces may be coated or covered with a material, e.g., mesh, silicone, etc., to further increase the frictional resistance against the tissue. Alternatively, the dissector arm surfaces may be roughened or patterned with projections to mechanically increase tissue resistance. In yet another variation, the arms may be coated with drug such as antibiotics, anti-thrombin agents, etc., to facilitate tissue healing after dissection.

Figure 12:
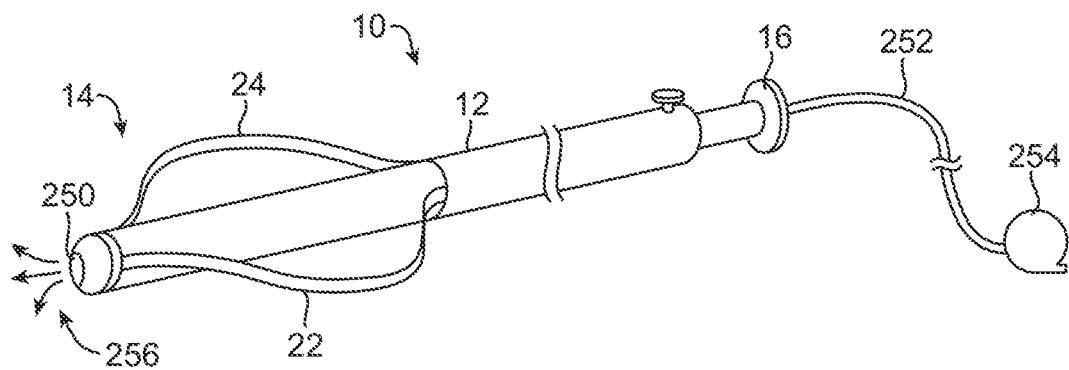
FIG. 12 shows another variation of the tissue dissector assembly having an integrated pumping mechanism to provide for insufflation and/or fluid injection through the assembly.

In yet another variation of the tissue dissector assembly 10, FIG. 12 shows an example in which a pump 254 may be fluidly connected to assembly 10 via fluid line 252 to provide for insufflation/exsufflation of a gas or fluid 256 (e.g., air, carbon dioxide, saline, water, etc.) directly through elongate body 12. This gas or fluid may be used before, during, or after mechanical dissection to alternatively initiate, enhance, or support dissection or to maintain or expand a dissected space. One or more fluid channels may be routed through elongate body 12 to a respective port or opening 250 located along assembly 10 or at its distal end. In another variation, one fluid channel may be dedicated as an insufflation port to enable insufflation during tissue dissection while a second fluid channel may be dedicated as a fluid delivery port.

Figure 13:
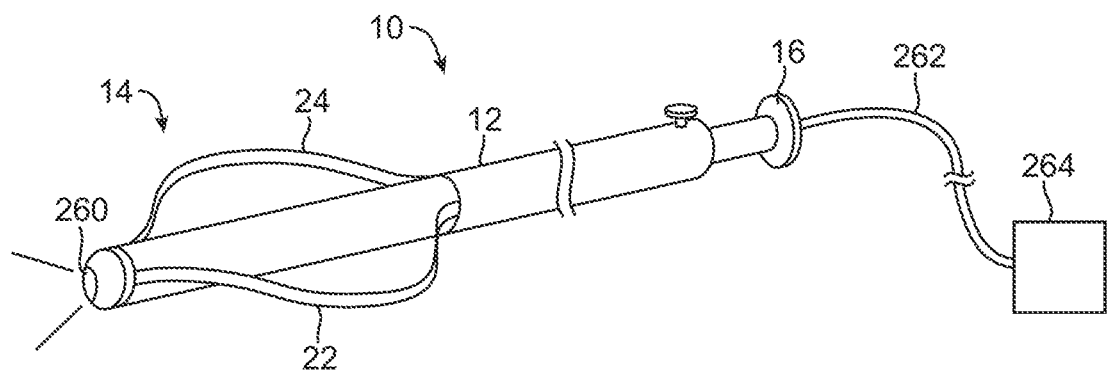
FIG. 13 shows yet another variation having an integrated video imaging assembly to provide visualization during insertion, dissection, or retraction into or from the patient body.

In another variation, FIG. 13 shows a perspective view of a tissue dissector assembly 10 having an additional viewing or imaging port 260 located at a distal end of assembly 10. The imaging port 260 may be alternatively located along elongate body 12 or even through one or more of dissector arm members 22, 24 to provide for visualization during insertion into the tissue, during dissection, and/or during retraction into or from the patient body. A cable 262 may be coupled to assembly 10 and routed to a video processor 264 for processing any images for display. Any number of conventional imaging modalities may be utilized as desired, e.g., CCD chips, fiber optic imaging fibers, etc., which may be inserted through elongate body 12 as a separate instrument or integrated directly with assembly 10.

Figure 14A:
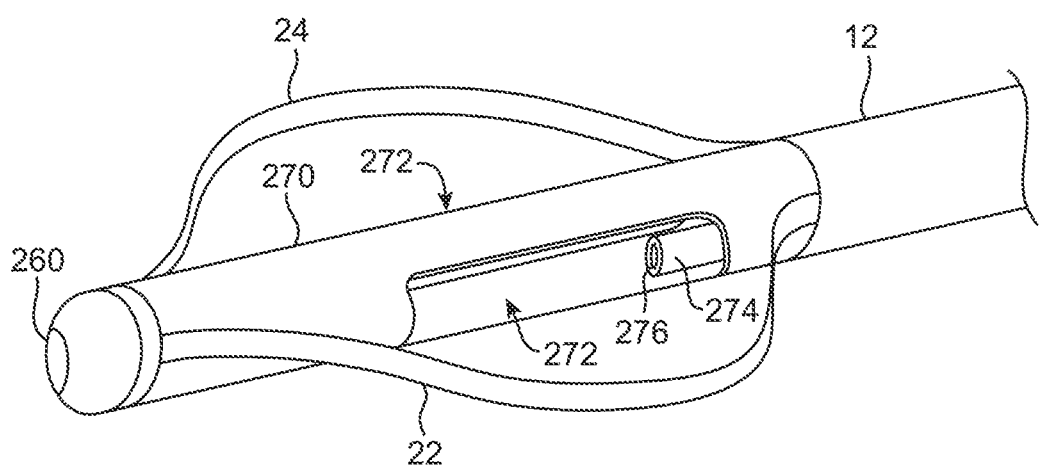
FIGS. 14A and 14B show detailed views of yet another variation where a video imaging system may be advanced through the tissue dissector assembly to provide direct visualization of the tissue region being dissected or retracted.
Figure 14B:
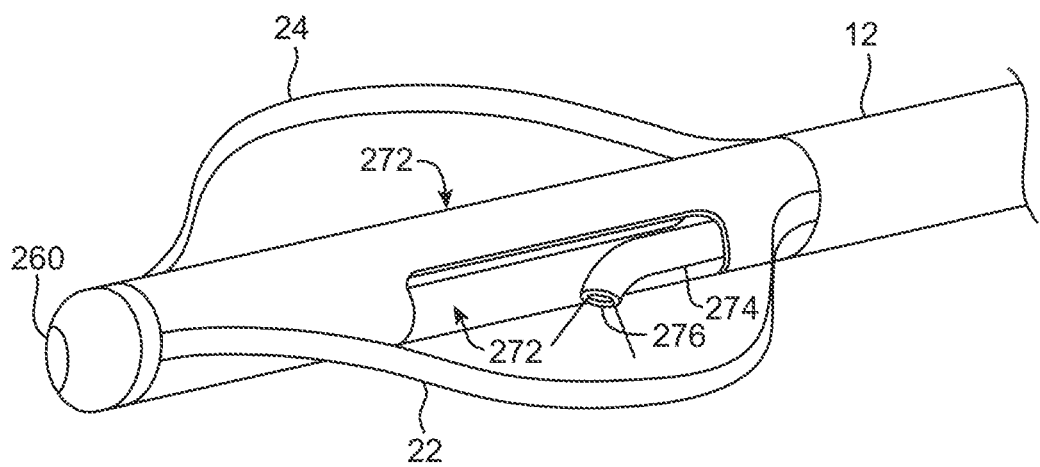

FIGS. 14A and 14B show detail perspective views of another alternative for providing visualization within the patient body during a procedure. In this variation, actuation shaft 270 may also serve as a viewing shaft by having one or more openings or slots 272 defined along its outer surface, as shown in FIG. 14A. These slots 272 may be defined on one or both sides of actuation shaft 270 adjacent to dissector arms 22, 24. During a procedure, a visualization instrument such as scope 274 having an imager 276 and a light source may be advanced through elongate body 12 and actuation shaft 270, as shown in FIG. 14A. Before, during, or after dissector arms 22, 24 are deployed into their expanded configuration, imager 274 may be pointed through either opening 272 to provide for visualization of the tissue being dissected or of the tissue region in general, as shown in FIG. 14B. As mentioned above, dissector arm members 22, 24 may be optionally configured to be translucent in which case the dissected tissue and/or surrounding tissue may be visualized directly through the translucent arm members 22, 24 from within the patient body utilizing imager 276.

Figure 15:
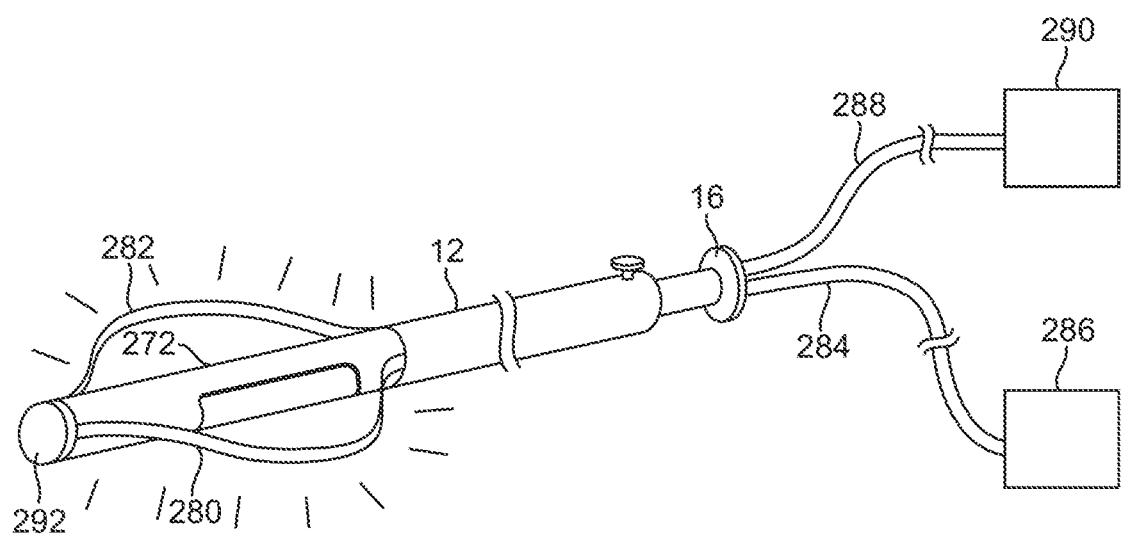
FIG. 15 shows yet another variation of the tissue dissector assembly where the dissector arms themselves may be configured to directly emit light to provide lighting during visualization.

In yet another variation, a light source may be provided through the assembly directly. Optical fibers may route the light emitted from an external light source 286 via light transmission cable 284 directly through elongate body 12 to aid visualization of the tissue region. An additional visualization instrument may be integrated or delivered through the assembly, as described above, while coupled via cable 288 to a video processor 290. Alternatively, an integrated light source 292 may be positioned along the assembly. Examples of integrated light sources may include, e.g., light emitting diodes. In yet another variation, dissector arm members 280, 282 may be fabricated from a light transmitting material, such as polycarbonate, which may transmit light directly from light source 286 to the surrounding tissue, as shown in FIG. 15. In such an embodiment, light transmitting arm members 280, 282 may not only provide a direct light source to the dissected and surrounding tissue, but the tissue may also be visualized directly through the translucent arm members 280, 282, as described above for FIG. 14B. Alternatively, light transmitting optical fibers may be routed directly through dissector arms 280, 282 to provide for light to the tissue.

Figure 16:
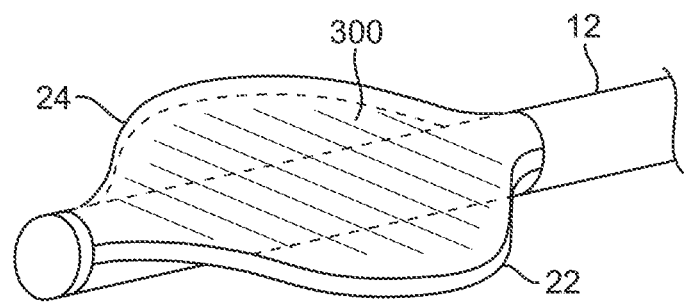
FIG. 16 shows yet another variation of the tissue dissector assembly having an optional distensible covering over the dissector arms for creating a surface for tissue retraction.
Figure 17:
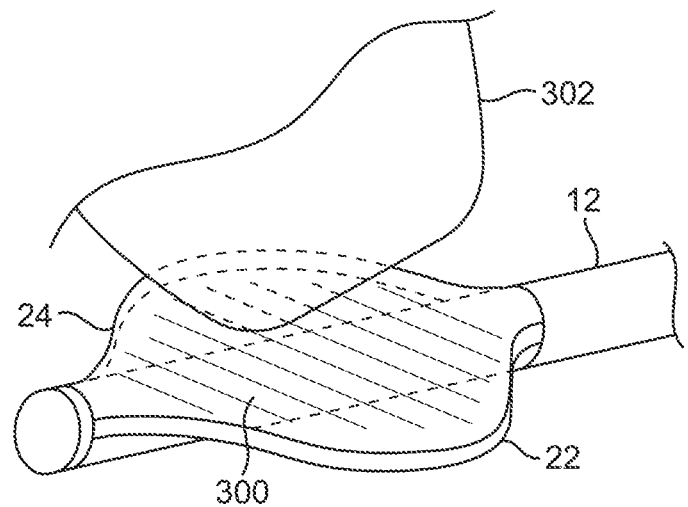
FIG. 17 shows the variation of the assembly of FIG. 16 being utilized to retract an organ within the patient body.

In another variation of the tissue dissector assembly, an optional covering or membrane 300, e.g., polyurethane, silicone, etc., may be disposed over dissector arms 22, 24 to form a surface which expands and retracts along with the arms, as shown in FIG. 16. Covering or membrane 300 may be utilized to facilitate use of the tissue dissector assembly for tissue or organ retraction along with the tissue dissection capabilities of the assembly. An example of the assembly for organ retraction is shown in FIG. 17, which shows the assembly retracting an organ 302, liver, bowel, fat, kidneys, etc., within the patient body. Tissue retraction may be performed without the covering, or membrane 300 at all and with dissector arms 22, 24 in any number of expanded configurations, i.e., fully or any number of intermediate expanded configurations.

The applications of the apparatus and methods discussed above are not limited to the disclosed features. Modification of the above-described assemblies and methods for carrying out the invention, and variations of aspects of the invention that are obvious to those of skill in the art are intended to be within the scope of the claims. Furthermore, various features of the dissector arms, visualization, lighting, etc., may be combined with one another in any number of combinations as practicable and are intended to be within the scope of this disclosure.

What is claimed:

1. A tissue manipulation assembly, comprising:
an elongate body shaft;
an actuation member movable relative to the elongate body shaft; and
a first arm member and a second arm member each having at least a distal end attached to a distal tip of the elongate body shaft via a pivot or pinned connection, wherein each arm member is positioned along the elongate body shaft opposite to one another such that each arm member reconfigures radially whereby each arm member is correspondingly configured within a single plane from a low profile to an expanded curved or arcuate planar profile when urged via the actuation member such that the assembly reconfigures along the single plane,
wherein each arm member is further positioned along the elongate body shaft such that each arm member is reconfigurable from the low profile where an entirety of each arm member resides against the elongate body shaft and into an overextended arcuate configuration extending distally beyond the assembly such that each arm member presents a curved outer surface located distally beyond where the distal end of each arm member is attached to the distal tip of the elongate body shaft and where the overextend arcuate configuration is shaped to inhibit bending of the overextended arcuate configuration outside the single plane, and
wherein each arm member has a feature which increases frictional resistance against tissue contacting the arm members.

2. The tissue manipulation assembly of claim 1 wherein the tissue manipulation assembly is configured for tissue retraction.

3. The tissue manipulation assembly of claim 1 wherein the tissue manipulation assembly is configured for tissue dissection.

4. The tissue manipulation assembly of claim 1 further comprising a handle assembly coupled to a proximal end of the elongate body shaft for actuating a reconfiguration of each arm member.

5. The tissue manipulation assembly of claim 4 wherein the handle assembly is adapted to actuate each arm member in a plurality of intermediate configurations between the low profile and the expanded curved or arcuate planar profile.

6. The tissue manipulation assembly of claim 1 wherein each arm member is adapted to simultaneously reconfigure within the single plane from the low profile to the expanded curved or arcuate planar profile.

7. The tissue manipulation assembly of claim 1 wherein each arm member defines a tapered or arcuate outer surface.

8. The tissue manipulation assembly of claim 1 wherein the feature comprises a coating or covering which increases the frictional resistance.

9. The tissue manipulation assembly of claim 1 wherein the elongate body has a non-uniform cross-section along its length.

10. The tissue manipulation assembly of claim 1 wherein the elongate body comprises a section which is configured to receive the arm members such that a low profile cross-section is presented for insertion into a body.

11. A tissue manipulation assembly, comprising:
an elongate body shaft;
an actuation member movable relative to the elongate body shaft; and
at least one arm member having a distal end attached to a distal tip of the elongate body shaft via a pivot or pinned connection,
wherein the at least one arm member is positioned along the elongate body shaft such that the at least one arm member reconfigures radially whereby the at least one arm member is configured within a single plane from a low profile to an expanded curved or arcuate planar profile when urged via the actuation member such that the assembly reconfigures along the single plane,
wherein the at least one arm member is further positioned along the elongate body shaft such the at least one arm member is reconfigurable from the low profile where an entirety of the at least one arm member resides against the elongate body shaft and into an overextended arcuate configuration extending distally beyond the assembly such that each arm member presents a curved outer surface located distally beyond where the distal end of each arm member is attached to the distal tip of the elongate body shaft and where the overextend arcuate configuration is shaped to inhibit bending of the overextended arcuate configuration outside the single plane, and
wherein the at least one arm member has a feature which increases frictional resistance against tissue contacting the at least one arm member.

12. The tissue manipulation assembly of claim 11 further comprising a handle assembly coupled to a proximal end of the elongate body shaft for actuating a reconfiguration of the at least one arm member.

13. The tissue manipulation assembly of claim 12 wherein the handle assembly is adapted to actuate the at least one arm member in a plurality of intermediate configurations between the low profile and the expanded curved or arcuate planar profile.

14. The tissue manipulation assembly of claim 11 wherein the at least one arm member defines a tapered or arcuate outer surface.

15. The tissue manipulation assembly of claim 11 wherein the a feature comprises a coating or covering which increases the frictional resistance.

* * * * *